United States Patent [19]

Dorr

[11] Patent Number: 4,627,841
[45] Date of Patent: Dec. 9, 1986

[54] INFUSION NEEDLE

[76] Inventor: Robert T. Dorr, 1130 S. Avenida Conalea, Tucson, Ariz. 85748

[21] Appl. No.: 830,076

[22] Filed: Feb. 18, 1986

[51] Int. Cl.$^4$ ............................................. A61M 5/18
[52] U.S. Cl. .................................... 604/158; 604/165
[58] Field of Search ................................. 604/51–53, 604/117, 156–158, 161, 164–165; 128/305

[56] References Cited

U.S. PATENT DOCUMENTS

| | | | |
|---|---|---|---|
| 1,527,291 | 2/1925 | Zorraquin | 604/158 |
| 2,842,133 | 7/1958 | Uhma | 604/158 |
| 3,659,610 | 5/1972 | Cimber | 604/158 |
| 3,786,810 | 1/1974 | Pannier, Jr. et al. | 604/158 |
| 3,840,008 | 10/1974 | Noiles | 604/158 |
| 4,068,660 | 1/1978 | Beck | 604/158 |
| 4,292,970 | 10/1981 | Hession, Jr. | 604/158 |
| 4,559,041 | 12/1985 | Razi | 604/157 |

*Primary Examiner*—C. Fred Rosenbaum
*Assistant Examiner*—Michelle N. Lester
*Attorney, Agent, or Firm*—Marshall, O'Toole, Gerstein, Murray & Bicknell

[57] ABSTRACT

A venipunture or similar infusion device comprises a blunt-ended catheter telescopically received in a sharp-tipped hollow needle, the catheter and needle being connected respectively to associated hubs which are spring-biased toward each other. In passive condition, with the hubs substantially in contact, the blunt end of the catheter protrudes from the sharp tip of the needle. For insertion of the device into a vein or other tissue, a wedge attached to one of the hubs is manipulated to wedge the hubs, and the catheter and needle attached thereto, a sufficient distance apart to cause the sharp tip of the needle to protrude beyond the blunt end of the catheter. After insertion, release of the wedge permits the spring to return the hubs to passive condition, with the blunt end of the catheter protruding from the sharp tip of the needle. Thus, during the indwelling period, the sharp tip of the needle is effectively covered and can do no damage to a vein or other tissue in which it is inserted.

5 Claims, 6 Drawing Figures

INFUSION NEEDLE

BACKGROUND OF THE INVENTION

A significant problem encountered during the administration of intravenous solutions to patients in hospitals, particularly over extended periods of time, is leakage of the intravenous fluid from the vein into which it is introduced. This leakage usually results from internal laceration of the vein by an indwelling catheter or butterfly needle having a sharp tip. Subsequent leakage of solution and soft tissue damage can become a major problem if the drug being introduced into the vein is a local irritant or soft tissue vesicant.

Sharp-tipped steel scalp-vein or "butterfly" needles having flexible wings which can be taped in position on the skin of a patient are commonly used for continuous subcutaneous and intravenous medication delivery. For subcutaneous infusions, the sharp tip of the needle can cause prolonged local irritation and pain which is compounded by the possibly irritant nature of the drug to hinder proper drug absorption.

SUMMARY OF THE INVENTION

The present invention overcomes the disadvantages of the intravenous and subcutaneous infusion devices heretofore known, by providing an assembly in which the sharp point of the needle is exposed or uncovered only for insertion of the assembly into the vein or other tissue of a patient and is automatically covered or retracted as soon as the insertion has been completed.

The device includes a blunt-ended catheter telescopically received in a sharp-tipped needle, the catheter and needle being connected respectively to associated hubs which are spring-biased toward each other. In passive condition, with the hubs substantially in contact, the blunt end of the catheter protrudes from the sharp tip of the needle. For insertion of the device into a vein or other tissue, wedge means are manipulated to wedge the hubs, and the catheter and needle attached thereto, a sufficient distance apart to cause the sharp tip of the hneedle to protrude beyond the blunt end of the catheter. After insertion, release of the wedge means permits the spring to return the hubs to passive condition, with the blunt end of the catheter protruding from the sharp tip of the needle. Thus, during the indwelling period, the sharp tip of the needle is effectively covered and can do no damage to a vein or other tissue in which it is inserted. In a preferred embodiment, the device of the invention includes wings of the conventional type, on which the wedge means are mounted, which facilitate taping the needle assembly into position on the skin of a patient.

DESCRIPTION OF THE DRAWINGS

The invention will be described with reference to the detailed description which follows considered in conjunction with the attached drawings in which.

DESCRIPTION OF A PREFERRED EMBODIMENT

Figure 1:
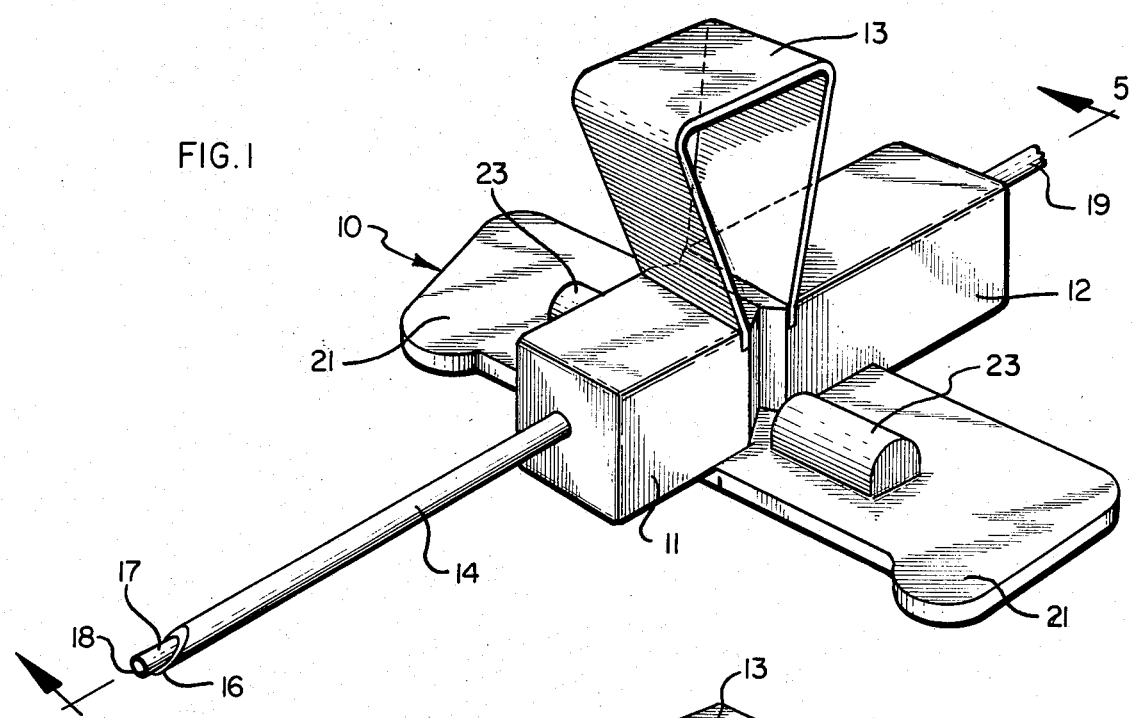
FIG. 1 is a perspective view of the needle assembly of the invention in passive condition, as it would exist either before or after insertion into a vein.

A preferred embodiment of the invention, shown generally at 10 in FIG. 1, comprises a front or needle hub 11 and a rear or catheter hub 12 interconnected by an open, generally triangular spring 13, the open ends of which are attached to hubs 11 and 12 to bias the hubs toward each other to adjacent positions.

A hollow needle 14 having a sharp tip 16 at one of its ends is attached at its other end to front hub 11. Telescopically positioned within hollow needle 14 is a rigid catheter 17 having two blunt ends, one end 18 of which is positioned in the vicinity of the sharp tip 16 of needle 14, the other end 19 of catheter 17 being exposed for attachment of a suitable conduit, e.g., plastic intravenous tubing (not shown), or any appropriate fitting such as a Luer-lock receptacle for supplying or receiving a fluid to or from the assembly.

The outer diameter of catheter 17 and the inner diameter of needle 14 are selected to provide a close fit, permitting telescoping movement of the elements to be readily affected while at the same time inhibiting inward or outward fluid leakage between the catheter and the needle.

In the passive condition shown in FIG. 1, the length of the section of catheter 17 which is within hollow needle 14 is such that blunt end 18 of the catheter protrudes slightly beyond sharp tip 16 of needle 14. Accordingly, in this condition, the sharp tip of the needle is in effect covered or retracted and incapable of penetrating any tissue that it might contact.

Figure 2:
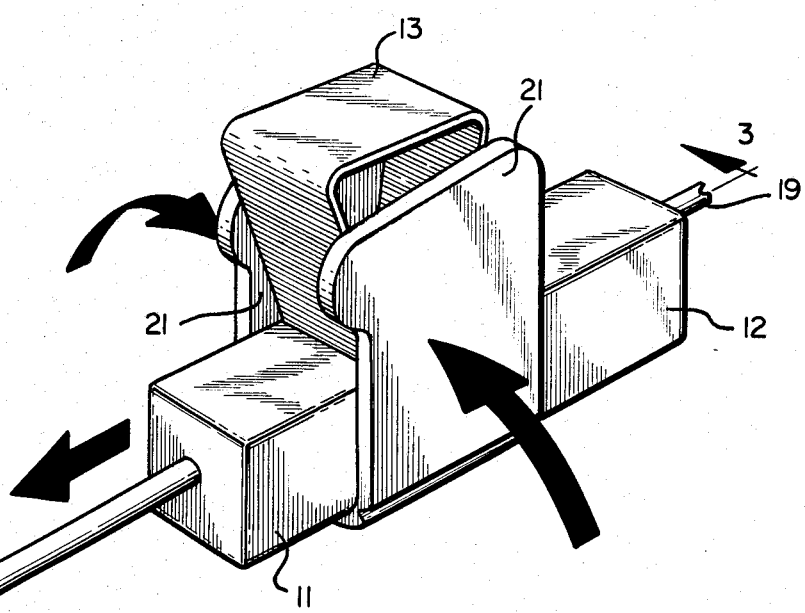
FIG. 2 is a view similar to that of FIG. 1 in which the flexible wings of the assembly have been folded or pinched together to expose the sharp pointed needle for insertion.

Attached to rear hub 12 are a pair of oppositely extending "butterfly" wings 21 suitably formed of a resilient plastic material and optionally provided with grooves 22 (FIG. 2) for facilitating the manual folding of the wings into the position shown in FIG. 2.

Carried on the upper surfaces of each of wings 21 is a wedge 23 or similar means positioned in the vicinity of the junction between front and rear hubs 11 and 12 and adapted, when the wings are manually folded and pinched together as in FIG. 2, to wedge front hub 11 away from rear hub 12 against the restoring force exerted by spring 13.

Figure 4:
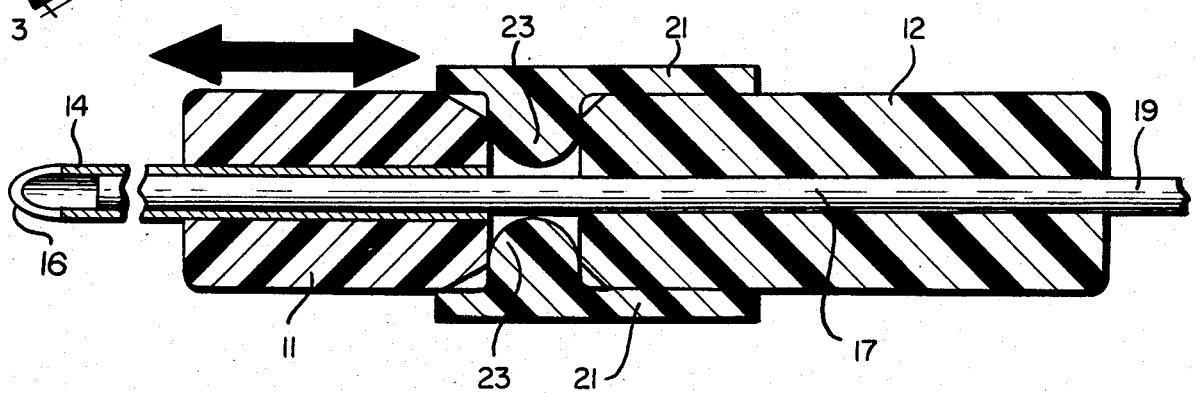
FIG. 4 is a cross-sectional view along the line 4—4 of FIG. 3 with the wings folded.
Figure 3:
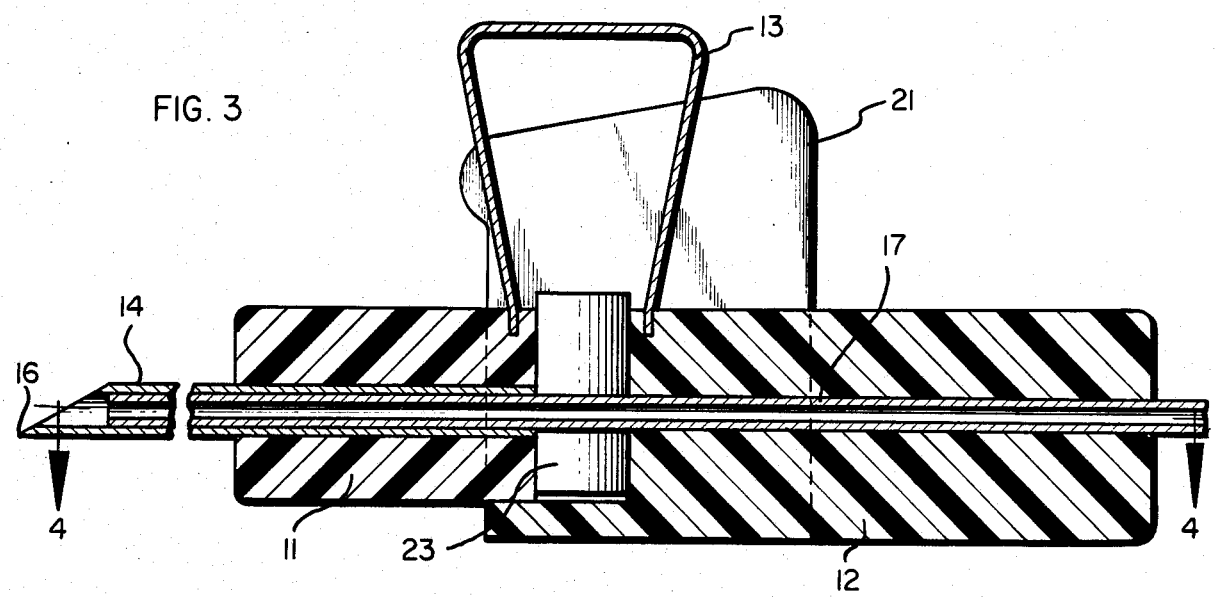
FIG. 3 is a cross-sectional view along the line 3—3 of FIG. 2 with the wings folded and the sharp tip of the needle exposed.
Figure 5:
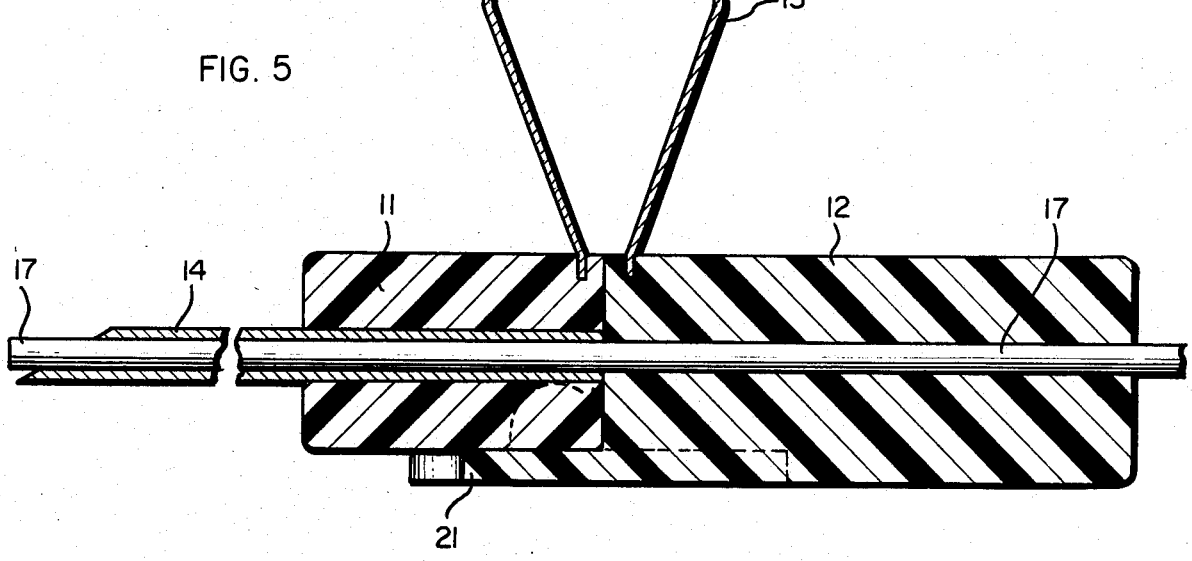
FIG. 5 is a cross-sectional view along the line 5—5 of FIG. 1 with the wings extended and the sharp tip of the needle covered.

When wings 21 are folded as shown in FIGS. 2, 3 and 4, wedges 23 are forced between front and rear hubs 11 and 12. Since catheter 17 and wings 21 are both attached to rear hub 12, no relative movement of these elements occurs. Front hub 11 and hollow needle 14 attached thereto, however, are free to move and are displaced laterally a distance equal to the width of wedges 23, sufficient to cause sharp tip 16 of needle 14 to extend beyond blunt end 18 of catheter 17, in position for inserting the assembly into a vein or other tissue. After the insertion has been made, release of wings 21 will permit spring 13 to retract needle 14 sufficiently so that sharp tip 16 thereof is no longer exposed. The extended wings can then be used to tape or otherwise secure the assembly to the body of a patient in conventional fashion.

While wings 21 have been described as being attached to rear hub 12 in the embodiment shown, it will be seen that they could alternatively be attached to front hub 11 leaving rear hub 12 free. In either event, folding and pinching the wings to cause insertion of wedges 23 between front and rear hubs 11 and 12 will cause relative longitudinal movement of the hollow needle and the rigid catheter, thus causing the sharp end of the needle to be exposed.

Figure 6:
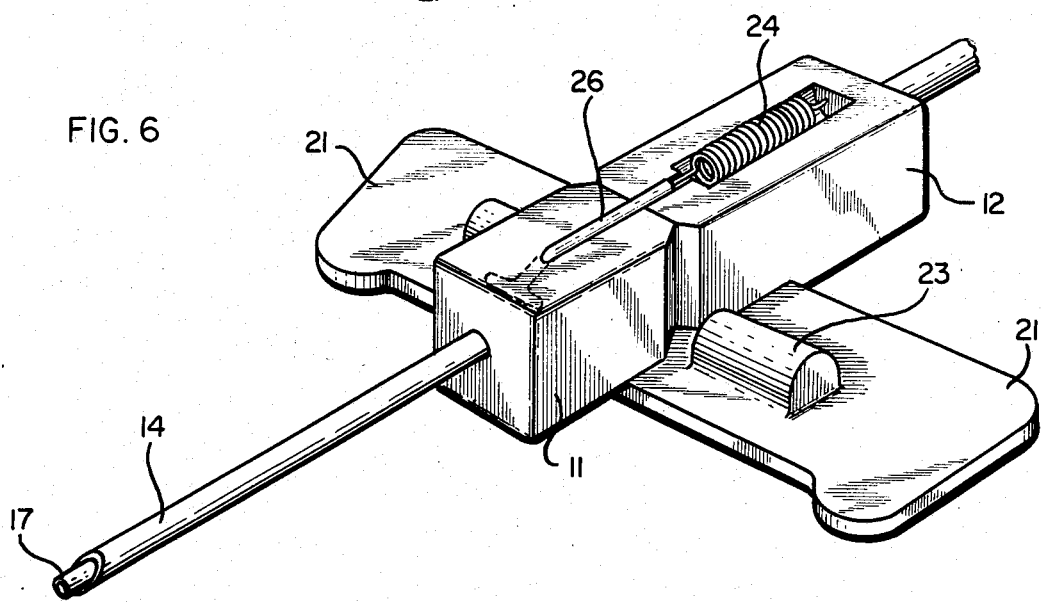
FIG. 6 is a perspective view of an assembly similar to that of FIG. 1 showing an alternative spring used for biasing the sections of the assembly.

As an alternative to the generally triangular open-ended spring 13 shown in FIG. 1, any other stuiable spring biasing arrangement can be used. In the alternative embodiment shown in FIG. 6, a helical spring 24, which can if desired be partially or totally recessed in either of hubs 11 and 12, is employed. The ends of spring 24 are effectively attached respectively to one of hubs 11 and 12, suitably by means of an extension 26.

The infusion device of the invention provides a number of advantages in use. Because in its passive state, i.e., when the wings are outwardly extended rather than pinched together, only the blunt end of the catheter can come into contact with the vein wall or other tissue, the risk of laceration or injury to a vein or other tissue in which the needle is inserted is greatly reduced. The apparatus of the invention is thus suitable for extended periods of use. Further, the fact that the assembly does not present a sharp end except when it is intentionally manipulated intentionally to do so, reduces the possibility of accidental injury or contamination to attending personnel during use or disposal of the apparatus.

The foregoing detailed description has been given for clearness of understanding only, and no unnecessary limitations should be understood therefrom as modifications will be obvious to those skilled in the art.

What is claimed is:

1. An infusion device comprising:
    a catheter having a blunt end;
    a catheter hub attached to said catheter and spaced from said blunt end;
    a hollow needle having a first end and a sharpened tip at a second end,
    a needle hub attached to said needle at said first end;
    said catheter being telescopically received in said needle with said needle hub adjacent said catheter hub,
    the telescoping respective lengths of said catheter and said needle being such that said blunt end of said catheter protrudes from said sharpened tip of said needle when said hubs are in contact;
    spring means interconnecting and biasing said hubs toward each other; and
    wedge means mounted on one of said hubs and insertable between said hubs to separate said hubs against the restoring force exerted by said spring means a distance sufficient to cause said sharpened tip of said needle to protrud beyond said blunt end of said catheter.

2. A device in accordance with claim 1 further including a pair of oppositely extending wings flexibly connected to one of said hubs.

3. A device in accordance with claim 2 in which said wedge means are mounted on at least one of said wings in position to separate said hubs when said wings are folded.

4. A device in accordance with claim 1 wherein said spring means is an open generally triangular member having its ends attached respectively to one of said hubs.

5. A device in accordance with claim 1 wherein said spring means is a coil spring substantially recessed in one of said hubs and having its ends operatively attached respectively to one of said hubs.

* * * * *